(12) United States Patent
Tarczynski et al.

(10) Patent No.: US 6,653,535 B1
(45) Date of Patent: Nov. 25, 2003

(54) METHODS FOR MODULATING WATER-USE EFFICIENCY OR PRODUCTIVITY IN A PLANT BY TRANSFORMING WITH A DNA ENCODING A NAPD-MALIC ENZYME OPERABLY LINKED TO A GUARD CELL OR AN EPIDERMAL CELL PROMOTER

(75) Inventors: Michell C. Tarczynski, West Des Moines, IA (US); Marianne M. Laporte, Ames, IA (US); Bo Shen, Johnston, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/321,991

(22) Filed: May 28, 1999

(51) Int. Cl.$^7$ .............................. A01H 5/00; C12N 15/82
(52) U.S. Cl. ..................... 800/320.1; 435/419; 435/468; 800/278; 800/298; 800/306; 800/312; 800/314; 800/317.4; 800/320; 800/287; 800/320.2; 800/320.3; 800/322
(58) Field of Search ................................. 800/278, 287, 800/298, 312–322; 435/468, 419

(56) References Cited

U.S. PATENT DOCUMENTS 5,538,879 A * 7/1996 Muller-Rober et al.

FOREIGN PATENT DOCUMENTS

| EP | 0 212 649 B1 | 8/1986 |
| EP | 0 874 056 A1 | 1/1998 |
| WO | WO 94/28180 | * 12/1994 |
| WO | WO 98/23757 | 6/1998 |
| WO | WO 01/46447 A2 | 6/2001 |

OTHER PUBLICATIONS

Gehlen et al. Effects of altered phophoenolpyruvate carboxylase activities on transgenic C3 plant Solanum tuberosum. Plant Molecular Biology 32:831–848, 1996.*

Gallardo et al. Monocotyledonous C4 NADP+–malate dehydrogenase is efficiently synthesized, targeted to chloroplasts and processed to an active form in transgenic plante of the C3 dicotyledon tobacco. Planta 197(2):324–332. 1995.*

Furbank et al. Genetic manipulation of key photosynthetic enzymes in the C4 plant Flaveria bidents. Aust. J. Plant Physiol. 24:477–485. 1997.*

Drincovich et al 2000, NADP–malic enzyme from plants: a ubiquitous enzyme involved in different metabolic pathways. FEBS Letters Vol 490, pp. 1–6.*

Outlaw et al. 1979, Guard cell starch concentration quantitatively related to stomatal aperture. Plant Physiology 64:79–81.*

Outlaw et al. 1977, Organic acid and potassium accumulation in guard cells during stomatal opening. Proc. Natl. Acad. Sci. USA 74(10):4434–4438.*

Van Kirk et al., Presence of Chloride Reduces Malate Production in Epidermis During Stomata Opening, Plant Physiol., 1978, pp. 361–364, vol. 61.

Raschke et al., Availability of Chloride Affects the Balance between Potassium Chloride and Potassium Malate in Guard Cells of *Vicia faba* L., Plant Physiol., 1978, pp. 84–87, vol. 62.

Outlaw , Jr. et al, High Levels of Malic Enzyme Activities in *Vicia faba* L. Epidermal Tissue, Plant Physiol., 1981, pp. 1047–1051, vol. 68.

Farquhar et al., Stomatal Conductance and Photosynthesis, Ann. Rev. Plant Physiol., 1982, pp. 317–345, vol. 33, Annual Reviews Inc..

Zeiger, E., The Biology of Stomatal Guard Cells, Ann. Rev. Plant Physiol., 1983, pp. 441–475, vol. 34, Annual Reviews, Inc.

Schnabl et al., Determination of Malate Levels During the Swelling of Vacuoles Isolated from Guard–Cell Protoplasts, Planta, 1984, pp. 27–31, vol. 161, Planta.

Birkenhead et al., Some Biochemical Characteristics of Guard Cell and Mesophyll Cell Protoplasts from *Commelina Communis* L., Journal of Experimental Botany, Jan. 1986, pp. 119–128, vol. 37, No. 174, Oxford University Press.

Jones H.G., Breeding for Stomatal Characters, Stomatal Function, 1987, pp. 440–443, Stanford University Press, Stanford, California USA.

Rademacher et al., New Synthetic Analogues of Abscisic Acid: Their Influence on Water Consumption and Yield Formation in Crop Plants, Structural and Functional Responses to Environmental Stresses, 1989, pp. 147–154, SPB Academic Publishing by, The Hague, The Netherlands.

Scheibe et al., Malate Dehydrogenases in Guard Cells of *Pisum Sativum*, Plant Physiol., 1990, pp. 1358–1364, vol. 93.

Tarczynski et al., The Interactive Effects of pH, 1–Malate, and Glucose–6–Phosphate on Guard–Cell Phosphoenolpyruvate Carboxylase, Plant Physiol., 1993, pp. 1189–1194, vol. 103.

Gehlen, et al., Effects of Altered Phosphoenolypyruvate Carboxylase Activities on Transgenic C3 plant *Solanum Tuberosuml*, 1996, Plant Molecular Biology, pp. 831–848, vol. 32, Kluwer Academic Publishers, Belgium.

Talbott et al, Central Roles for Potassium and Sucrose in Guard–Cell Osmoregulation, Plant Physiol., 1996, pp. 1051–1057, vol. 111.

(List continued on next page.)

Primary Examiner—Amy J. Nelson
Assistant Examiner—David H Kruse
(74) Attorney, Agent, or Firm—Alston & Bird LLP

(57) ABSTRACT

A method for modulating water-use efficiency or productivity in a plant is provided. In particular, stomatal aperture in a plant can be regulated by transforming the plant with a polynucleotide that encodes a NADP-malic enzyme operably linked to a guard cell or an epidermal cell promoter that modifies malate accumulation in the stomata.

25 Claims, 7 Drawing Sheets

OTHER PUBLICATIONS

Du et al., In Vivo Phosphorylation of Phosphoenolpyruvate Carboxylase in Guard Cells of *Vicia faba* L. Is Enhanced by Fusicoccin and Suppressed by Abscisic Acid, Archives of Biochemistry and Biophysics, Jan. 15, 1997, pp. 345–350, vol. 337, No. 2, Article No. BB969790, Academic Press.

Kopka et al., Potato Guard Cells Responding to Drying Soil by a Complex Change in the Expression of Genes Related to Carbon Metabolism and Turgor Regulation, The Plant Journal, 1997, pp. 871–882, vol. 11(4).

Grill et al, A Plant's Dilemma, Science, Oct. 9, 1998, pp. 252–253, vol. 282.

Ku et al, High–Level Expression of Maize Phosphoenolpyruvate Carboxylase in Transgenic Rice Plants, Nature Biotechnology, Jan. 1999, pp. 76–81, vol. 17.

Mann, Genetic Engineers Aim to Soup Up Crop Photosynthesis, Science, Jan. 15, 1999, pp. 314–316, vol. 233.

Mann, Crop Scientists Seek a New Revolution, Science, Jan. 15, 1999, pp. 310–316, vol. 283.

* cited by examiner

METHODS FOR MODULATING WATER-USE EFFICIENCY OR PRODUCTIVITY IN A PLANT BY TRANSFORMING WITH A DNA ENCODING A NAPD-MALIC ENZYME OPERABLY LINKED TO A GUARD CELL OR AN EPIDERMAL CELL PROMOTER

FIELD OF THE INVENTION

The invention is drawn to genetic engineering of plants to improve agronomic performance, particularly for increasing water-use efficiency in plants.

BACKGROUND OF THE INVENTION

Plant growth is often limited by the availability of water. In plants, the majority of all water loss occurs through pores on the leaf surface, which are called stomata. The sizes of the stomatal pores in a leaf are variable and control the rate of diffusion of water vapor out of the plant. In addition to controlling water loss, stomata allow $CO_2$ to diffuse into the leaf for photosynthesis. This common pathway for gas exchange between the leaf and the atmosphere results in a large amount of water vapor escaping from the plant during the influx of $CO_2$. However, stomatal aperture is typically substantially greater than that needed for maintaining maximal photosynthetic rates.

Each stomate is formed by two guard cells. Together, the two guard cells form a stomatal pore. Opening and closing of stomata are caused by specialized biochemical processes in the guard cells that occur in response to environmental changes. The pore is opened by an increase in osmotic pressure in the guard cells, which is the result of the uptake and synthesis of osmotically active compounds and a corresponding uptake of water. The increase in guard-cell volume causes the pore to open.

To minimize water loss from leaves, stomatal aperture is regulated. During water shortage, plants prevent dehydration by closing their stomata partially or completely. When water is not limiting and other environmental conditions favor photosynthesis and plant growth, stomata are open, allowing $CO_2$ to enter for photosynthesis. Because plant growth is often limited by the availability of water and because the amount of water loss greatly exceeds $CO_2$ uptake necessary for photosynthetic carbon reduction, molecular mechanisms are needed to increase water-use efficiency in plants.

SUMMARY OF THE INVENTION

An object of the present invention is to provide methods and compositions for improving water-use efficiency in plants.

Another object of the present invention is to provide methods and compositions for increasing drought tolerance in plants.

Another object of the present invention is to provide methods and compositions for increasing irrigation efficiency.

Another object of the present invention is to provide methods and compositions for increasing productivity under conditions when water is not limiting.

Another object of the present invention is to provide methods and compositions for increasing heat tolerance in plants.

The methods comprise engineering a plant to modify malate accumulation in the plant to alter stomatal conductance to water vapor. Polynucleotides capable of modifying the accumulation of malate in the plant can be used in cassettes or constructs for expression in plants or plant cells of interest. Transformed plants, tissues, and seeds having improved water-use efficiency are provided.

Methods for modulating stomatal aperture or altering water-use efficiency in a plant are provided, the methods comprise:

a) transforming a plant cell with a polynucleotide operably linked to a promoter that drives expression in a plant, wherein the polynucleotide is capable of modulating malate accumulation in the plant cell, with the proviso that when the polynucleotide encodes phosphoenolpyruvate carboxylase, the plant is other than potato or tobacco;

b) regenerating plants from the transformed cell; and c) selecting for plants exhibiting an altered stomatal aperture or altered water-use efficiency or characteristic correlated to same.

Also provided are methods for increasing productivity in a plant comprising:

a) transforming a plant cell with a polynucleotide operably linked to a promoter that drives expression in a plant, wherein the polynucleotide is capable of modulating malate accumulation in the plant cell, with the proviso that when the polynucleotide encodes phosphoenolpyruvate carboxylase, the plant is other than potato or tobacco;

b) regenerating plants from the transformed cell; and c) selecting for regenerated plants exhibiting improved productivity.

DETAILED DESCRIPTION OF THE INVENTION

Figure 1:
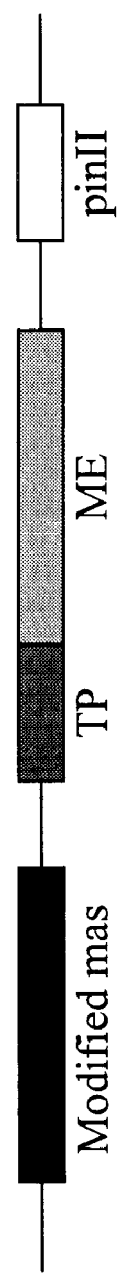
FIG. 1: Gene construct used in transformation examples.

The present invention is drawn to compositions and methods for modulating stomatal aperture in plants. In particular, methods of the invention are useful for increasing water-use efficiency in plants. Methods encompass transforming a plant with a polynucleotide capable of modulating malate accumulation in the plant. Typical enzymes that can modulate the level of malate include malic enzyme, malate dehydrogenase, phosphoenolpyruvate carboxylase, glycolytic enzymes, or starch degradation enzymes. As used herein, "a polynucleotide corresponding to" a particular enzyme means the polynucleotide is capable of altering the expression of the enzyme. The altered malate concentration leads to a change in guard-cell volume that alters stomatal pore size.

Polynucleotides useful in the invention encompass antisense or coding constructs for the enzymes of the invention. Thus, antisense sequences can be used to decrease expression of the enzyme. Likewise, coding sequences can be utilized to increase or decrease expression. Also single chain antibodies can be used to modulate the level of the enzymes.

As noted above, methods for modulating the stomatal aperture are provided. The benefits of modifying stomatal aperture are significant. For example, decreasing stomatal aperture is expected to improve drought tolerance. As water is a limited resource in many areas of the world, drought tolerance is a valuable trait. In the case of a well-watered crop, increasing the stomatal aperture is expected to improve heat tolerance and productivity.

Methods of the invention comprise expressing a polynucleotide capable of modulating the level of malate in a plant. A broad range of enzymes can influence the level of malate. Such enzymes include but are not limited NADP-malic enzyme (ME), malate dehydrogenase, phosphoenolpyruvate carboxylase, and enzymes of the pathway that convert starch—to malate, e.g., glycolytic and starch degrading enzymes. Thus, a plant may be transformed with one or a combination of the enzymes. Other polynucleotides capable of modulating the level of malate in a plant include those encoding malate or dicarboxylic transporter.

The nucleotide sequences encoding ME are known in the art. For example, $C_4$ NADP$^+$-ME full-length cDNAs have been cloned from several monocot and dicot species (e.g., AC#J05130, AC#J03825). There is NAD$^+$ malic enzyme as well. Additionally, other enzymes of interest are known and include malate dehydrogenase, phosphoenolpyruvate carboxylase, glycolytic enzymes such as, hexokinase, hexosephosphate isomerase, phosphofructokinase, aldolase, fructokinase, triose phosphate isomerase, glyceraldehyde 3-phosphate dehydrogenase, phosphoglycerate kinase, phosphoglycerate mutase, enolase, pyruvate kinase, and starch degrading enzymes such as α-amylase, β-amylase, starch phosphorylase, D enzyme, α-glucosidase, debranching enzyme, and α-1,4-glucan lyase. Examples of suitable polynucleotides encoding the enzymes can be found in the following cites: phosphofructokinase, *J. Biol. Chem.* 265 (30):18366–18371 (1990); The complete nucleotide sequence of cDNA encoding phosphoenolpyruvate carboxylase from cultured tobacco, *Plant Mol. Biol.* 17(3):535–540 (1991); triose-phosphate isomerase, *Mol. Biol. Evolution* 7(1):74–81 (1990); glyceraldehyde 3-phosphate dehydrogenase, *Plant Physiology (Rockville)* 105(1):357–367 (1994); pyruvate kinase, *Plant Physiology (Bethesda)* 96(4):1283–1288 (1991); fructokinase, *Plant Physiology (Bethesda)* 93(1):353–355 (1990); aldolase, *Plant Mol. Biol.* 21(2):331–340 (1993); NADP+-malate dehydrogenase, *Proceedings of the National Academy of Sciences of the United States of America* 92(12):5620–5624 (1995); enolase, *Plant Cell* 3(7):719–736 (1991); barley alpha-arnylase, *Applied-Microbiology-and-Biotechnology* 49(4):385–392 (1998); B-amylase, beta-amylase gene of Arabidopsis thaliana, *Plant Physiology (Rockville)* 114(2):575–582 (1997); starch phosphorylase, sequencing of the phosphorylase cDNA, *Plant Cell* 1(5):559–566 (1989); D-enzyme, from potato tubers and its activity characterized, *J. Biol. Chem.* 268(2):1391–1396 (1993); alpha-glucosidase, Bulletin of the Research Institute for Bioresources Okayama Univ. 5(1):1–9 (1997); a-Glucosidase, Bioscience Biotech. and Biochem. 57(11):1902–1905 (1993); starch debranching enzyme from developing rice endosperm: Purification, cDNA and chromosomal localization of the gene, Planta (Heidelberd) 199(2):209–218 (1996).

It is recognized that the sequences disclosed above may be used as well as variants or fragments thereof. Additionally, polynucleotides encoding variant proteins may be utilized. It is only important that the polynucleotide modulates the accumulation of malate in the plant, preferably in the leaves, and more preferably in the guard cells.

It is recognized that with these nucleotide sequences, antisense constructions, cosuppression or other method for down-regulation complementary to at least a portion of the messenger RNA (mRNA) for the target enzymes can be constructed. Antisense nucleotides are constructed to hybridize with the corresponding mRNA. Therefore, modifications of the sequences may be made as long as the sequences hybridize to and interfere with expression of the corresponding mRNA. In this manner, antisense constructions having 70%, preferably 80%, more preferably 85% sequence similarity to the corresponding antisense sequences may be used. Furthermore, portions of the antisense nucleotides may be used to disrupt the expression of the target gene. Generally, sequences of at least about 20, 30, 50 nucleotides, 100 nucleotides, 200 nucleotides, or greater may be used.

While the methods can be used in any plant the following crops are of particular interest, but are not limited to maize, sorghum, soybean, sunflower, safflower, alfalfa, canola, tomato, wheat, rice, peanut, and cotton.

The sequences to be introduced may be used in expression cassettes for expression in any plant of interest where expression in the plant is necessary for transcription. While it may be preferable to express the sequences using heterologous promoters, the native promoter sequences may be used. Such constructs would change expression levels of the enzymes of interest in the plant or plant cell. Thus, the phenotype of the plant or plant cell is altered.

Where expression cassettes are needed, such expression cassettes will comprise a transcriptional initiation region linked to the coding sequence or antisense sequence of the nucleotides of interest. Such an expression cassette is provided with a plurality of restriction sites for insertion of the sequence to be under the transcriptional regulation of the regulatory regions. The expression cassette may additionally contain selectable marker genes.

The transcriptional initiation region, the promoter, may be native or analogous or foreign or heterologous to the plant host. Additionally, the promoter may be a natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

The transcriptional cassette will include in the 5'-to-3' direction of transcription, a transcriptional and translational initiation region, a polynucleotide of interest, and a transcriptional and translational termination region functional in plants. The termination region may be native with the transcriptional initiation region, may be native with the polynucleotide of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell.* 2:1261–1272; Munroe et al. (1990) *Gene* 91:151–158; Ballas et al. (1989) *Nucleic Acids Res.* 17:7891–7903; Joshi et al. (1987) *Nucleic Acids Res.* 15:9627–9639. Additionally the 3' termination sequence (e.g., nopaline synthase or CaMV) can be used. The cassette may also contain at least one additional sequence to be co-transformed into the organism. Alternatively, the additional sequence(s) can be provided on another expression cassette.

In preparing the expression cassette, the various polynucleotide fragments may be manipulated, so as to provide for the polynucleotide of interest in the proper orientation and, as appropriate, in the proper reading frame. Toward this end, adapters or linkers may be employed to join the polynucleotide fragments or other manipulations may be involved to provide for convenient restriction sites, removal of superfluous sequences, removal of restriction sites, or the like. For this purpose, in vitro mutagenesis, primer repair, restriction, annealing, resubstitutions, e.g., transitions and transversions, may be involved.

A variety of promoters may be used in the practice of the invention. In particular, PCaMV35S plus enhancer (strong and constitutive), PrbcS (strong, leaf preferred), Pcab (strong, leaf preferred) and Pnos (weak and constitutive) can be used. Other promoters of interest include, the core promoter of the Rsyn7 (copending U.S. patent application Ser. No. 08/661,601), the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. patent application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142. Preferably guard cell or epidermal cell promoters, such as KAT1 (Nakamura et al. (1995) *Plant Physiology* 109:371–374, kin1, cor6.6 (Wang and Cutler (1995) *Plant Mol. Biol.* 28:619–634), the 0.3-kb 5' promoter fragment of ADPase (Müller-Röber et al. (1994) *Plant Cell* 6:601–612), Rha1 (Terryn et al. (1993) *Plant Cell* 5:1761–1769) are used. The use of drought inducible, guard-cell promoters, such as CdeT6-19 (Taylor et al. (1995) *Plant Journal* 7:129–134) would also be desirable.

The genes of interest of the present invention can be targeted to the chloroplast for expression. In this manner, where the gene of interest is not directly inserted into the chloroplast, the expression cassette will additionally contain a gene encoding a transit peptide to direct the gene of interest to the chloroplasts. Such transit peptides are known in the art. See, for example, Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res. Commun.* 196:1414–1421; and, Shah et al. (1986) *Science* 233:478–481. Chloroplast targeting sequences additionally include the chloroplast small subunit of ribulose-1,5-bisphosphate carboxylase (Rubisco), (de Castro Silva Filho et al. (1996) *Plant Mol. Biol.* 30:769–780; Schnell, et al. (1991) *J. Biol. Chem.* 266(5):3335–3342); 5-(enolpyruvyl) shikimate-3-phosphate synthase (EPSPS) (Archer et al. (1990) *J. Bioenerg. Biomemb.* 22(6):789–810); tryptophan synthase (Zhao et al. (1995) *J. Biol. Chem.* 270(11):6081–6087); plastocyanin (Lawrence et al. (1997) *J. Biol. Chem.* 272(33):20357–20363); chorismate synthase (Schmidt et al. (1993) *J. Biol. Chem.* 268(36):27477–27457); and the light harvesting chlorophyll a/b binding protein (LHBP) (Lamppa et al. (1988) *J. Biol. Chem.* 263:14996–14999). See also Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481. Additionally, the rbcS transit sequence can be used for targeting to the chloroplast stroma.

It is possible that direct chloroplast transformation could be used for expression of the enzymes of interest. Methods for transformation of chloroplasts are known in the art. See, for example, Svab et al. (1990) *Proc. Natl. Acad. Sci. USA* 87:8526–8530; Svab and Maliga (1993) *Proc. Natl Acad. Sci. USA* 90:913–917; Staub and Maliga (1993) *Embo J.* 12:601–606. The method relies on particle gun delivery of the polynucleotide of interest containing a selectable marker and targeting of the polynucleotide of interest to the plastid genome through homologous recombination. Additionally, plastid transformation can be accomplished by transactivation of a silent plastid-borne transgene by tissue-specific expression of a nuclear-encoded and plastid-directed RNA polymerase. Such a system has been reported in McBride et al. (1994) *Proc. Natl. Acad. Sci. USA* 91:7301–7305.

The sequences of the present invention can be used to transform or transfect any plant. In this manner, genetically modified plants, plant cells, plant tissue, seed, and the like can be obtained. Transformation protocols as well as protocols for introducing nucleotide sequences into plants may vary depending on the type of plant or plant cell, i.e. monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes et al. "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (1995) (maize); Klein et al. (1988) *Plant Physiol.* 91:440–444 (maize); Fromm et al. (1990) *Biotechnology* 8:833–839 (maize); Hooydaas-Van Slogteren and Hooykaas (1984) *Nature (London)* 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418; and Kaeppler et al. (1992) *Theor. Appl. Genet.* 84:560–566 (whisker-mediated transformation); D☐Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The modified plant may be grown into plants in accordance with conventional ways. See, for example, McCormick et al. (1986) *Plant Cell. Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

In practicing the present invention, the malate content generally will be modulated by at least about 5%, frequently at least about 10%, preferably at least about 15%, more preferably in the range of from about 15% to about 65%, and most preferably in the range of from about 15% to about 45%.

Using the methods of the present invention, the stomatal conductance is modulated at least about 5%, preferably at least about 10%, more preferably in the range of from about 15% to about 80%, and most preferably in the range of from about 15% to about 65%. As indicated above, the stomatal conductance will be reduced where increased water efficiency is desired. In order to increase heat stress tolerance, stomatal conductance will be increased.

Generally the present methods can be employed to increase water-use efficiency by at least about 5%, preferably at least about 10% and more preferably in the range of from 10% to 20%.

The following examples are offered by way of illustration and not by way of limitation.

EXAMPLES

A cDNA sequence encoding $C_4$ NADP$^+$-malic enzyme (ME) from maize (AC#J05130) was fused to a cDNA sequence encoding an rbcS chloroplast transit peptide from petunia (Dean et al. (1987) *Nucleic Acids Res.* 15:4655–4668), a modified mas promoter (Ni et al. (1995) *Plant Journal* 7:661–676), and a pinII terminator (An et al. (1989) *Plant Cell* 1:115–122; FIG. 1). The modified mas promoter directs expression in a variety of plant tissues, including leaf epidermal cells and guard cells. The ME gene construct was linked to the nptII gene, which confers kanamycin resistance for use as a selectable marker (Herrera-Estrella et al. (1983) *EMBO J.* 2:987–995). The expression cassette was cloned into the pBK-CMV expression vector (Stratagene, Inc.).

Gene constructs were introduced into tobacco by Agrobacterium-mediated transformation (Horsch et al. (1985) *Science* 227:1229–1231; An et al. (1986) *Plant Physiol.* 81:301–305). More than 10 kanamycin resistant transformation events were regenerated.

Figure 2:
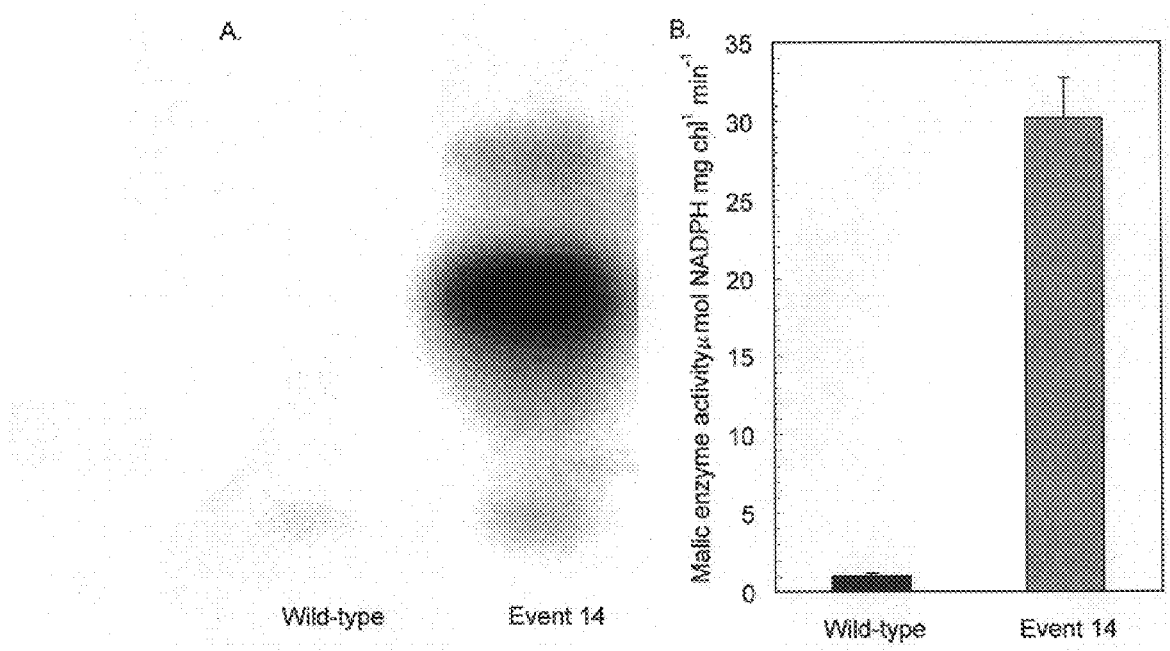
FIG. 2A: Northern blots depicting maize malic enzyme mRNA for wild-type and transformed tobacco leaves.
FIG. 2B: Malic enzyme activity in wild-type and transformed tobacco leaves.
Figure 3:
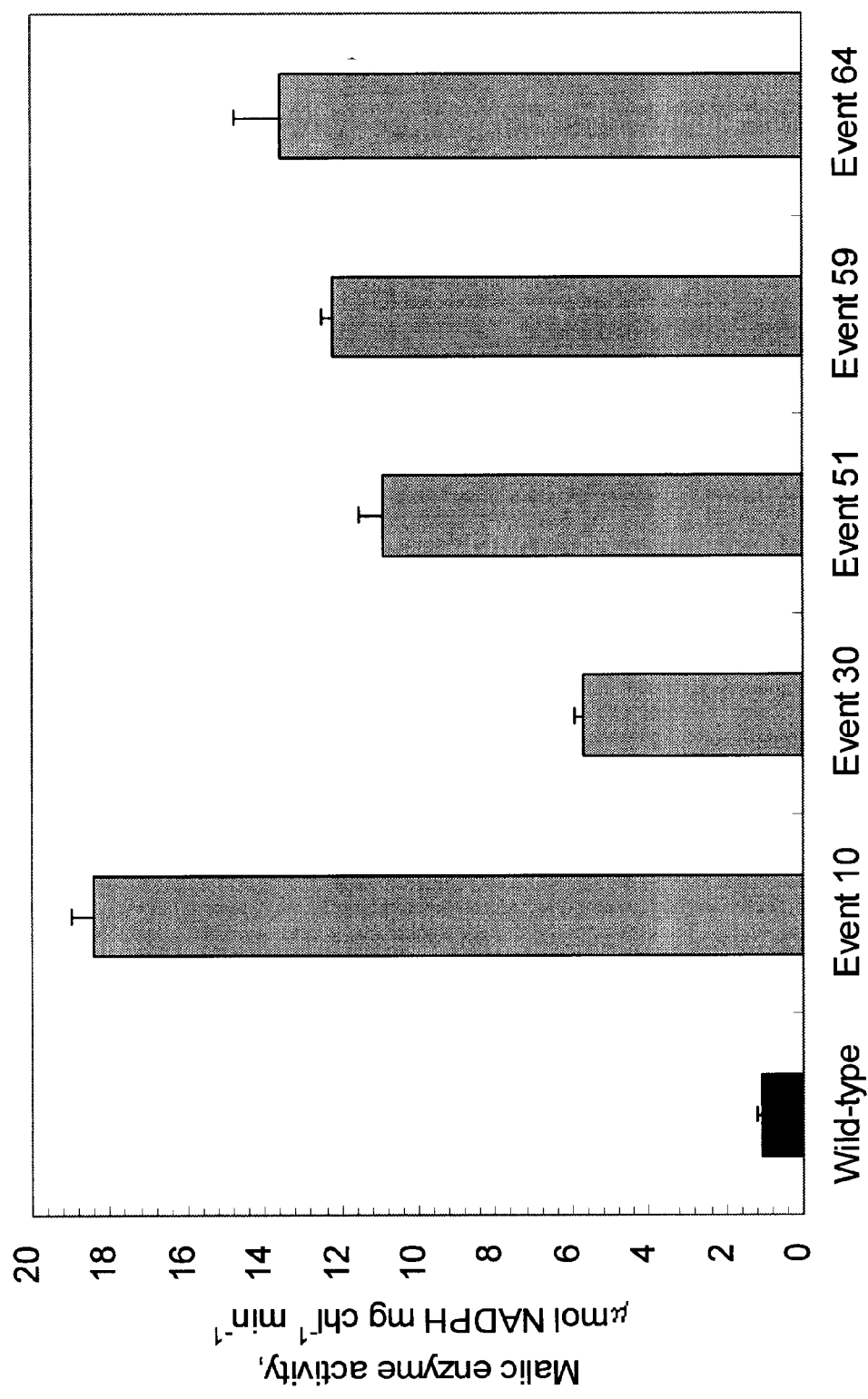
FIG. 3: Malic enzyme activity in wild-type and transformed tobacco leaves.

Maize ME mRNA transcript accumulated to high levels in the transgenic events, as demonstrated by the representative northern blot shown in FIG. 2A. A maize ME gene specific probe was used to assay for the presence of mRNA encoding maize ME. Total extractable ME activity was increased as much as 30 fold in the ME-transformed events relative to wild-type tobacco (FIG. 2B). Malic enzyme activity was assayed as described by Kanai and Edwards (1973) *Plant Physiol.* 51:1133–1137. The selfed progeny of the five events depicted in FIG. 3 were used for phenotypic analysis. Homozygous individuals from these events had ME activity ranging from 5 to 18 times that of wild-type tobacco in young leaves. Individuals containing one or two copies of the ME gene as well as null segregants derived from these events were analyzed after two generations of selfing ($T_2$ generation). All data depicted in the figures are from individuals with two copies of the gene except as noted.

Figure 4:
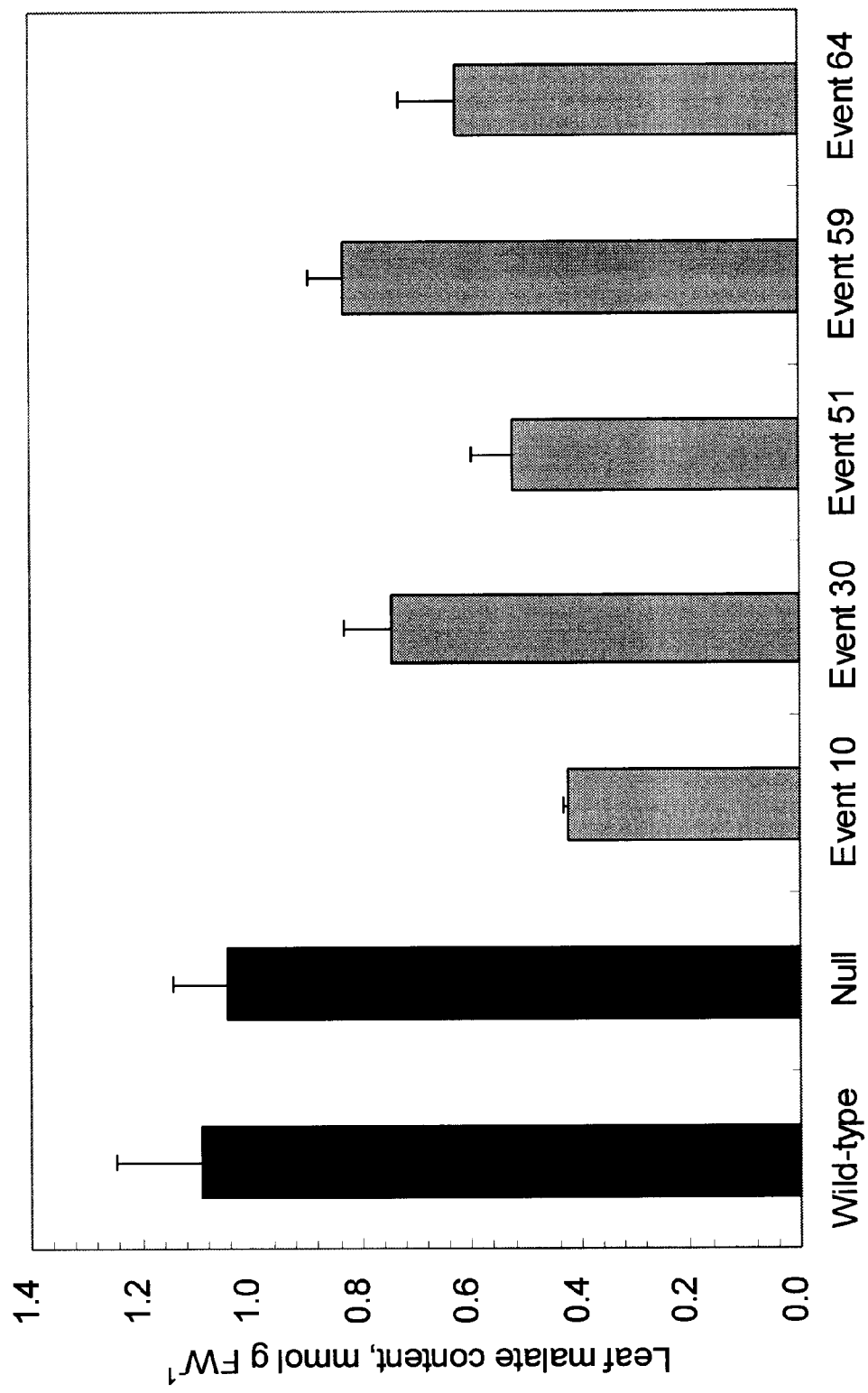
FIG. 4: Malate content in wild-type and transformed tobacco leaves.

Whole-leaf malate content was decreased by 23 to 61% in the ME-transformed plants relative to wild-type and null segregants (FIG. 4). Whole-leaf malate content was assayed as described by Ku et al. (1981) *Plant Physiol.* 68:1073–1080. It is likely that this decrease in whole-leaf malate is correlated with a decrease in guard-cell malate because the modified mas promoter is known to express in both guard and epidermal cells (Ni et al. (1995) *Plant Journal* 7:661–676).

Figure 5:
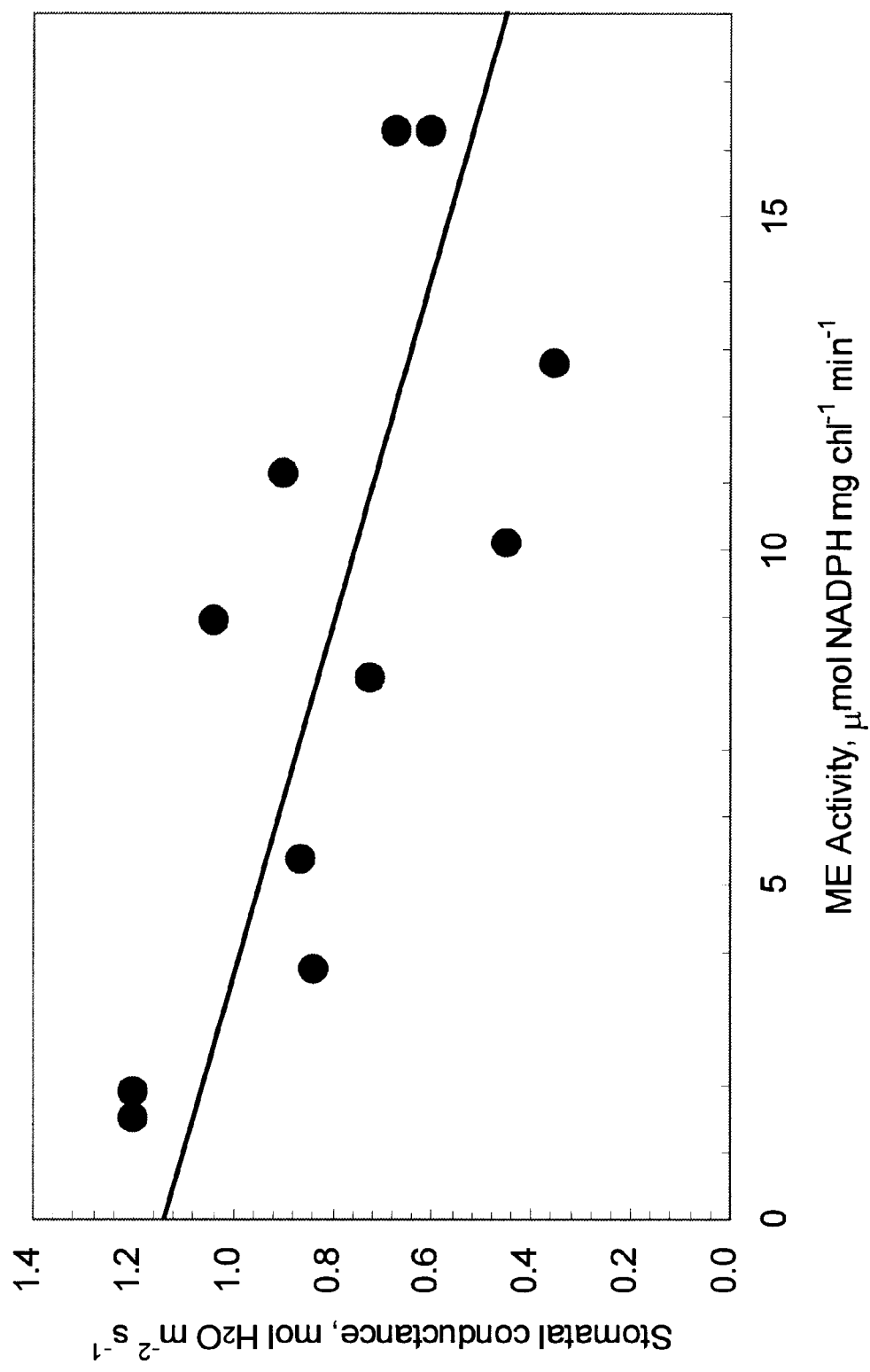
FIG. 5: Steady-state stomatal conductance in wild-type and transformed tobacco leaves.

Steady-state stomatal conductance to water vapor was significantly negatively correlated with total extractable ME activity in a segregating population that included individuals derived from all five transgenic events and wild-type ($F_{1,9}$=1.49; P=0.013; FIG. 5). Stomatal conductance was measured in attached, fully expanded leaves using a LiCor 6400 Portable Photosynthesis System equipped with the 6400-02B LED light source (LiCor, Inc., Lincoln Nebr.). Measurement of steady-state stomatal conductance was performed by continuously monitoring stomatal conductance under 1200 $\mu$mol photons m$^{-2}$ s$^{-1}$ of light, 25° C., and constant relative humidity. After 30 minutes of steady state conductance, the conductance value was recorded.

Figure 6:
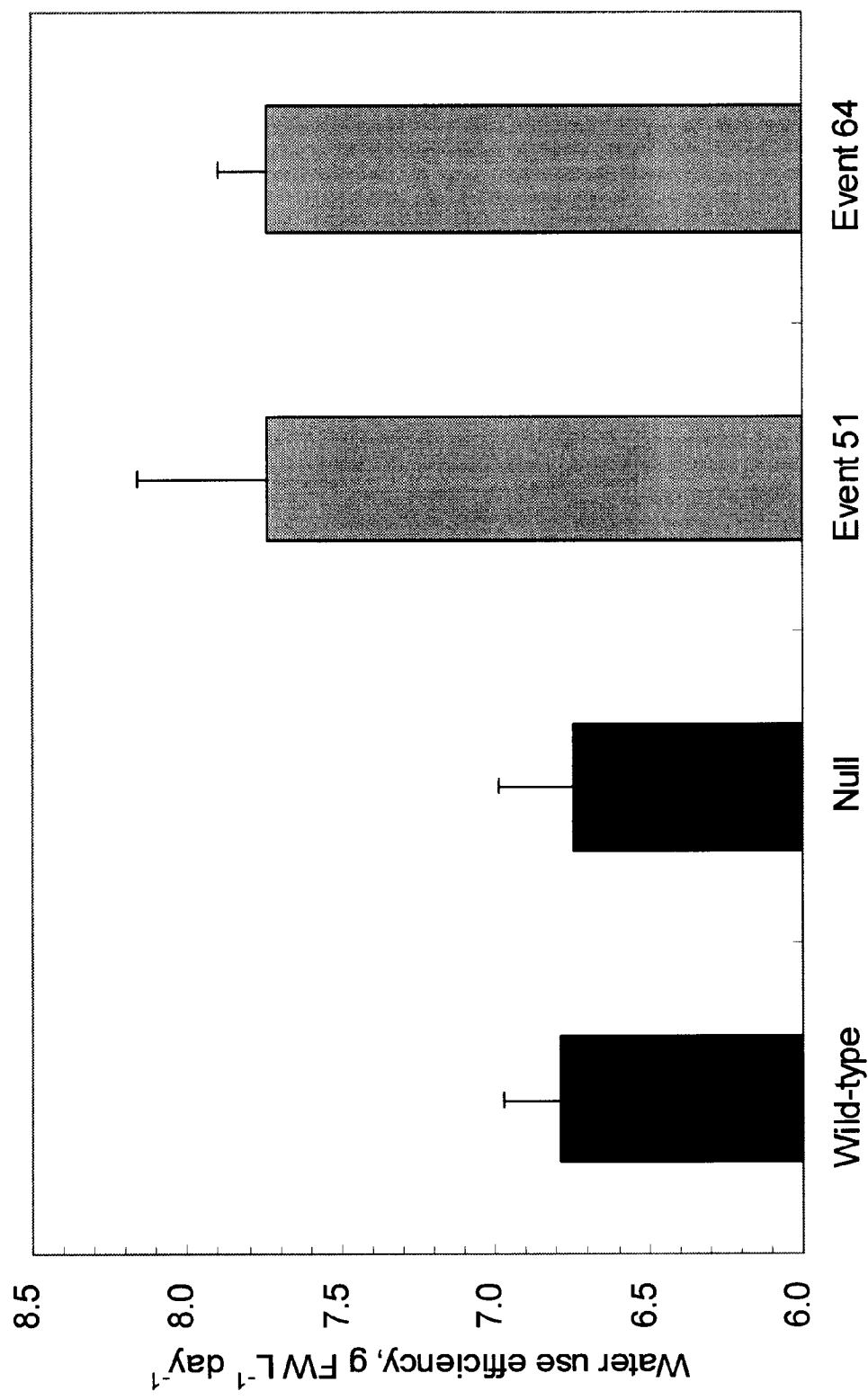
FIG. 6: Water-use efficiency in wild-type and transformed tobacco plants.

Water-use efficiency was significantly increased in the ME-transformed plants relative to null segregants and wild-type tobacco (FIG. 6). Neither the rate of growth nor the root-shoot ratio differed significantly among the ME-transformants, null segregants or wild-type under these conditions (data not shown). The plants were grown in ½ strength Hoagland's solution in a Conviron growth chamber equipped with incandescent and florescent lights that provided 400 $\mu$mol photons m$^{-2}$ s$^{-1}$ at plant level, 25/20° C., and 60% relative humidity. The volume of the solution was measured and the plants were gently patted dry and weighed daily.

Figure 7:
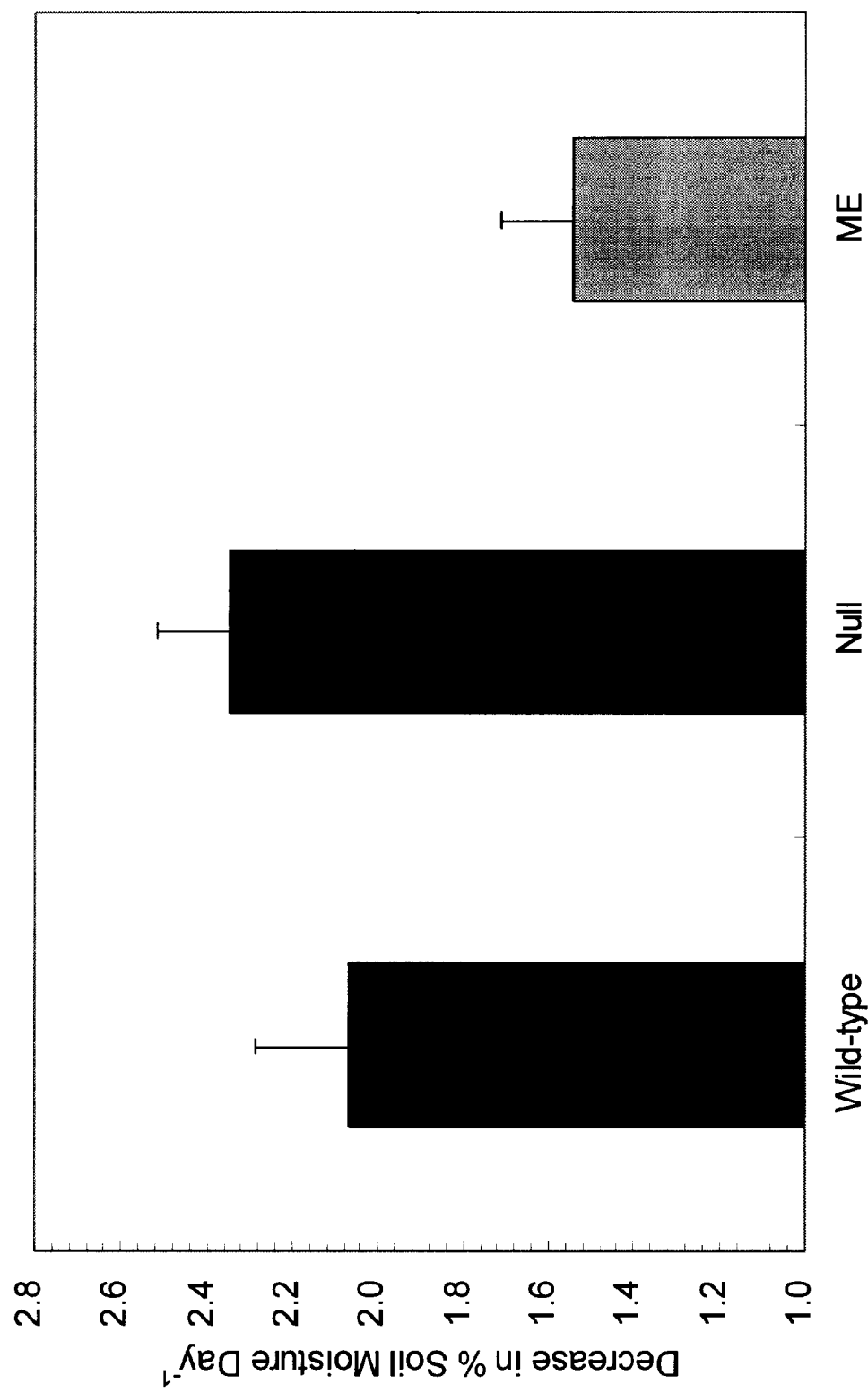
FIG. 7: Drought response of wild-type and transformed tobacco plants.

Under conditions of limited water availability, the wild-type and null segregants lost soil moisture more rapidly than the ME-transformed plants (FIG. 7). The plants were grown in 1 L pots and watered twice daily from below for 15 minutes per watering. Percent soil moisture was calculated as described by Pei et al. (1998) *Science* 282:287–290. Under these conditions, wilting of the ME-transformed plants was delayed relative to wild-type or null segregants (data not shown).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for decreasing steady-state stomatal conductance in a plant comprising:
   a) transforming a plant cell with a polynucleotide operably linked to a promoter that drives expression in a plant cell, wherein said polynucleotide encodes NADP-malic enzyme and wherein the expression of said polynucleotide decreases malate accumulation in the plant cell;

b) regenerating plants from the transformed cell; and c) selecting for regenerated plants having a decrease in steady-state stomatal conductance or an increase in water-use efficiency, wherein said promoter is a guard cell promoter or an epidermal cell promoter.

2. The method of claim 1, wherein said polynucleotide is operably linked to a DNA sequence encoding a transit peptide.

3. The method of claim 1, wherein said plant is selected from the group consisting of maize, soybean, sorghum, sunflower, alfalfa, canola, safflower, tomato, wheat, rice, peanut, and cotton.

4. The method of claim 3, wherein said plant is maize.

5. The method of claim 3, wherein said plant is soybean.

6. A method for increasing water-use efficiency in a plant comprising:

a) transforming a plant cell with a polynucleotide operably linked to a promoter that drives expression in a plant cell, wherein said polynucleotide encodes NADP-malic enzyme and wherein the expression of said polynucleotide decreases malate accumulation in the plant cell;

b) regenerating plants from the transformed cell; and c) selecting for regenerated plants having a decrease in steady-state stomatal conductance or an increase in water-use efficiency, wherein said promoter is a guard cell promoter or epidermal cell promoter.

7. The method of claim 6, wherein said polynucleotide is operably linked to a DNA sequence encoding a transit peptide.

8. The method of claim 6, wherein said plant is selected from the group consisting of maize, sorghum, soybean, sunflower, alfalfa, canola, safflower, tomato, wheat, rice, peanut, and cotton.

9. The method of claim 8, wherein said plant is maize.

10. The method of claim 9, wherein said plant is soybean.

11. A transformed plant comprising an isolated polynucleotide stably integrated into the plant genome, wherein;

a) said polynucleotide is operably linked to a promoter that drives expression in a plant cell;

b) said polynucleotide encodes NADP-malic enzyme;

c) the expression of said polynucleotide decreases the level of malate in the plant cell;

d) the plant has a decrease in steady-state stomatal conductance or an increase in water-use efficiency as compared to an untransformed plant; and e) said promoter is a guard cell promoter or an epidermal cell promoter.

12. The plant of claim 11, wherein the malate level is decreased by at least about 5%.

13. The plant of claim 11, wherein the malate level is decreased by at least about 10%.

14. The plant of claim 11, wherein the malate level is decreased from about 15% to about 65%.

15. The plant of claim wherein stomatal conductance is decreased at least about 5%.

16. The plant of claim 11, wherein stomatal conductance is decreased at least about 10%.

17. The plant of claim 11, wherein stomatal conductance is decreased from about 15% to about 80%.

18. The plant of claim 11, wherein stomatal conductance is decreased from about 15% to about 65%.

19. The plant of claim 11, wherein water-use efficiency is increased by at least about 5%.

20. The plant of claim 11, wherein water-use efficiency is increased by at least about 10%.

21. The plant of claim 11, wherein water-use efficiency is increased in the range of from about 10% to about 20%.

22. The plant of claim 11, wherein said polynucleotide is operably linked to a DNA sequence encoding a transit peptide.

23. The plant of claim 11, wherein said plant is selected from the group consisting of maize, sorghum, soybean, sunflower, safflower, alfalfa, canola, tomato, wheat, rice, peanut, and cotton.

24. The plant of claim 23, wherein said plant is maize.

25. The plant of claim 23, wherein said plant is soybean.

* * * * *

UNITED STATES PATENT AND TRADEMARK OFFICE
CERTIFICATE OF CORRECTION

PATENT NO. : 6,653,535 B1  
DATED : November 25, 2003  
INVENTOR(S) : Tarczynski et al.

Page 1 of 1

It is certified that error appears in the above-identified patent and that said Letters Patent is hereby corrected as shown below:

Title page,  
Item [54], Title, "NAPD" should read -- NADP --.  
Item [56], References Cited, OTHER PUBLICATIONS, insert the following:  
-- Ni et al., Strength and Tissue Specificity of Chimeric Promoters Derived from the Otopine and Mannopine Synthase Genes, *The Plant Journal*, 1995, pp. 661-676, Vol. 7 (4).  
Kogami et al., Molecular and Phsiological Evaluation of Transgenic Tobacco Plants Expressing a Maize Phosphoenolpyruvate Carboxylase Gene Under the Control of the Cauliflower Mosaic Virus 35S Promoter, *Transgenic Research*, 1994, pp. 287-296.  
Rothermel et al., Primary Structure of the Maize NAPD-Dependent Malic Enzyme, *The Journal of Biological Chemistry*, 1989, pp. 19587-19592, Vol. 264 (33). --.

Item [75], Inventors, first inventor's name "Michell" should read -- Mitchell --.

Column 9,  
Line 8, begin new sub-paragraph with -- wherein --,  
Line 31, begin new sub-paragraph with -- wherein --,  
Line 41, "claim 9" should read -- claim 8 --.

Column 10,  
Line 19, "claim" should read -- claim 11 --.

Signed and Sealed this

Fifteenth Day of June, 2004

JON W. DUDAS  
*Acting Director of the United States Patent and Trademark Office*

UNITED STATES PATENT AND TRADEMARK OFFICE
CERTIFICATE OF CORRECTION

PATENT NO. : 6,653,535 B1
DATED : November 25, 2003
INVENTOR(S) : Tarczynski et al.

It is certified that error appears in the above-identified patent and that said Letters Patent is hereby corrected as shown below:

Title page,
Item [56], References Cited, OTHER PUBLICATIONS, delete the following:
"Ni et al., Strength and Tissue Specificity of Chimeric Promoters Derived from the Otopine and Mannopine Synthase Genes, *The Plant Journal*, 1995, pp. 661-676, Vol. 7 (4).
Kogami et al., Molecular and Phsiological Evaluation of Transgenic Tobacco Plants Expressing a Maize Phosphoenolpyruvate Carboxylase Gene Under the Control of the Cauliflower Mosaic Virus 35S Promoter, *Transgenic Research*, 1994, pp. 287-296.
Rothermel et al., Primary Structure of the Maize NAPD-Dependent Malic Enzyme, *The Journal of Biological Chemistry*, 1989, pp. 19587-19592, Vol. 264 (33)."

Signed and Sealed this

Seventh Day of September, 2004

JON W. DUDAS
*Director of the United States Patent and Trademark Office*